(12) United States Patent
Yasukawa

(10) Patent No.: US 7,615,106 B2
(45) Date of Patent: Nov. 10, 2009

(54) AIR CONDITIONING APPARATUS

(75) Inventor: Akihiro Yasukawa, Katsuragi (JP)

(73) Assignee: Sharp Kabushiki Kaisha, Osaka (JP)

( * ) Notice: Subject to any disclaimer, the term of this patent is extended or adjusted under 35 U.S.C. 154(b) by 114 days.

(21) Appl. No.: 11/995,896

(22) PCT Filed: Jul. 18, 2006

(86) PCT No.: PCT/JP2006/314164

§ 371 (c)(1),
(2), (4) Date: Jan. 16, 2008

(87) PCT Pub. No.: WO2007/010894

PCT Pub. Date: Jan. 25, 2007

(65) Prior Publication Data

US 2009/0100850 A1 Apr. 23, 2009

(30) Foreign Application Priority Data

Jul. 22, 2005 (JP) ............................. 2005-213280

(51) Int. Cl.
*B03C 3/68* (2006.01)

(52) U.S. Cl. ..................... 96/18; 96/19; 96/26; 96/57; 96/63; 422/120

(58) Field of Classification Search ............ 96/18, 96/19, 25, 26, 57, 58, 63, 95–97; 95/2, 3, 95/69, 78; 422/5, 120
See application file for complete search history.

(56) References Cited

U.S. PATENT DOCUMENTS

| | | | | |
|---|---|---|---|---|
| 3,495,381 A | * | 2/1970 | Flanagan | 96/63 |
| 4,811,197 A | * | 3/1989 | Wexler | 700/47 |
| 5,035,728 A | * | 7/1991 | Fang | 96/19 |
| 5,616,172 A | * | 4/1997 | Tuckerman et al. | 96/16 |
| 5,632,806 A | * | 5/1997 | Galassi | 96/16 |
| 5,667,563 A | * | 9/1997 | Silva, Jr. | 96/50 |
| 5,759,487 A | * | 6/1998 | Jung | 422/22 |
| 5,814,135 A | * | 9/1998 | Weinberg | 96/58 |
| 5,865,880 A | * | 2/1999 | Matsui | 96/26 |
| 6,355,095 B1 | * | 3/2002 | Kuo-Long | 96/26 |
| 6,508,982 B1 | * | 1/2003 | Shoji | 422/22 |
| 6,623,544 B1 | * | 9/2003 | Kaura | 95/3 |
| 6,955,708 B1 | * | 10/2005 | Julos et al. | 95/59 |
| 7,285,155 B2 | * | 10/2007 | Taylor et al. | 96/25 |
| 2001/0029728 A1 | * | 10/2001 | Massey et al. | 55/471 |

(Continued)

FOREIGN PATENT DOCUMENTS

JP       59-134440 A   *   8/1984   ................. 96/26

(Continued)

*Primary Examiner*—Richard L Chiesa
(74) *Attorney, Agent, or Firm*—Birch, Stewart, Kolasch and Birch, LLP

(57) ABSTRACT

A control device repeats first air volume control and second air volume control for a predetermined number of times irrespective of a control state at that time while forcedly driving an ion generator, when a bacteria elimination shower switch is turned on. In the first air volume control, a sirocco fan generates an air flow having a predetermined air volume. In the second air volume control, the sirocco fan generates an air flow having an air volume smaller than the predetermined air volume. Therefore, a bacteria elimination effect is enhanced in an air conditioning apparatus.

6 Claims, 10 Drawing Sheets

U.S. PATENT DOCUMENTS

2004/0123739 A1 * 7/2004 Jan .............................. 96/18
2007/0022879 A1 * 2/2007 Aiba ............................ 95/58

FOREIGN PATENT DOCUMENTS

| JP | 4-187253 A * | 7/1992 | ............ 96/97 |
|----|----|----|----|
| JP | 9-180585 A | 7/1997 | |
| JP | 9-210433 A | 8/1997 | |
| JP | 9-247773 A | 9/1997 | |
| JP | 2000-121111 A | 4/2000 | |
| JP | 2002-78788 A | 3/2002 | |
| JP | 2004-44903 A | 2/2004 | |
| JP | 2004-89260 A | 3/2004 | |
| JP | 2004-100998 A | 4/2004 | |
| JP | 2004-101125 A | 4/2004 | |
| JP | 2004-293893 A | 10/2004 | |
| JP | 2005-27744 A | 2/2005 | |
| JP | 3949146 B2 | 4/2007 | |

* cited by examiner

MIDDLE AIR VOLUME

SMALL AIR VOLUME

AIR CONDITIONING APPARATUS

This application is the national stage of International Application No. PCT/JP2006/314164, filed on Jul. 18, 2006.

TECHNICAL FIELD

The present invention relates to an air conditioning apparatus for purifying air in a room.

BACKGROUND ART

Conventionally, there is used an air conditioning apparatus for eliminating bacteria in air of a room. The air conditioning apparatus includes an ion generator for generating ions and a blower for generating an air flow let out along with the ions. The air conditioning apparatus eliminates airborne bacteria and the like in the air of the room by the ions.

Patent Document 1: Japanese Patent Laying-Open No. 9-180585
Patent Document 2: Japanese Patent Laying-Open No. 9-210433
Patent Document 3: Japanese Patent Laying-Open No. 9-247773
Patent Document 4: Japanese Patent Laying-Open No. 2000-121111

DISCLOSURE OF THE INVENTION

Problems to be Solved by the Invention

In the conventional air conditioning apparatus, to enhance a bacteria elimination effect, it is necessary to control adjustment of an air volume of the blower. However, because it is not clear how the blower needs to be controlled in order to enhance the bacteria elimination effect, there is no air conditioning apparatus for performing specific control to intentionally enhance the bacteria elimination effect.

In view of the foregoing, an object of the present invention is to provide an air conditioning apparatus for performing the specific control to enhance the bacteria elimination effect.

Means for Solving the Problems

An air conditioning apparatus according to the present invention includes an ion generator for generating ions; a flow path forming member incorporating the ion generator and causing air to flow therethrough; a blower for causing the air to flow through the flow path forming member; an air outlet disposed in an end portion of the flow path forming member to blow the ions along with the air flowing in the flow path forming member; a control device for controlling the ion generator and the blower; and a bacteria elimination shower switch to perform running in a bacteria elimination shower mode having a predetermined high bacteria elimination effect, wherein the control device controls the blower such that the air having an air volume within a predetermined range is generated irrespective of a control state at that time while the ion generator is forcedly driven, when the bacteria elimination shower switch is turned on.

In the above-described configuration, when the bacteria elimination shower switch is turned on, the air flow having the air volume suitable for enhancement of the bacteria elimination effect is automatically generated, so that the bacteria elimination effect can be improved.

Preferably the air conditioning apparatus further includes a filter to be able to collect a pollution substance in the air, wherein the blower sucks the air through the filter and causes the air to flow into the flow path forming member after the pollution substance is removed by the filter, and the control device controls the blower such that the blower generates the air flow having an air volume smaller than a maximum air flow the blower can generate.

In the control of the air conditioning apparatus, in general a large air volume is desirably generated by the blower in consideration of a pollution substance removing effect. However, in the above-described control, the control device controls such that the blower generates the air flow having the air volume daringly smaller than the maximum air volume the blower can generate. Therefore, because disappearance of the air including the ions blown from the air outlet due to collision of the air with a ceiling or a wall is suppressed, the ions blown from the air outlet easily fall to the floor surface without disappearance, thereby enhancing the bacteria elimination effect. Further, when the blower is controlled to generate the maximum air flow the blower can generate, it is possible to enhance the pollution substance removing effect. That is, a user can select and perform either the control for enhancing the pollution substance removing effect or the control for enhancing the bacteria elimination effect.

Further, the control device preferably controls the blower such that the blower generates the air flow having an air volume larger than a minimum air flow the blower can generate.

In the control of the air conditioning apparatus, in general a small air volume is desirably generated by the blower in consideration of a noise of the air conditioning apparatus. However, in the above-described control, the blower is controlled to generate the air flow having the air volume larger than the minimum air volume the blower can generate. Therefore, the amount of ions blown from the air outlet is prevented from decreasing less than the minimum amount for obtaining the appropriate bacteria elimination effect, so that the bacteria elimination effect is enhanced according to the above-described control. Running of the air conditioning apparatus is performed in the silent mode when the blower is controlled to generate the air flow having the minimum air volume the blower can generate. That is, the user can select and perform either the control for the silent mode or the control for the mode realizing the high bacteria elimination effect.

Further, the control device preferably performs first air volume control for causing the blower to generate the air flow having a predetermined air volume and second air volume control for causing the blower to generate the air flow having an air volume smaller than the predetermined air volume, when the bacteria elimination shower switch is turned on.

In the conventional air conditioning apparatus, the control is not performed such that the ions are blown while dispersed in the room. Accordingly, because the ions fall intensively to a predetermined position in the room, sometimes the bacteria elimination is performed only at the predetermined position in the room while hardly performed in other places. In other words, because the conventional air cleaner cannot evenly perform the bacteria elimination in the room, sometimes the bacteria elimination effect becomes decreased.

On the contrary, according to the control, in the bacteria elimination shower mode, the ions are blown out of air outlet while the air volume of the blower is automatically changed. That is, the ions are blown away from the air conditioning apparatus or fall near the air conditioning apparatus. In other words, the ions do not fall intensively to the predetermined position in the room, but the ions fall to a plurality of positions in a dispersed manner. Accordingly, the user can press only the bacteria elimination shower switch to easily perform the even bacteria elimination in the room. Additionally, when the control device repeats the first air volume control and the second air volume control, the bacteria elimination is more evenly performed in the room.

The air volume can automatically be changed to intensively perform the bacteria elimination of a region within a predetermined range in the room with the small air volume.

Further, the control device preferably performs control identical to control immediately before the bacteria elimination shower switch is turned on when running in the bacteria elimination shower mode is ended. In the control, even if the user does not manipulate any switch, the air conditioning apparatus automatically returns to a state immediately before the bacteria elimination shower switch is turned on, so that user's convenience can be improved.

When the bacteria elimination shower switch is larger than other switches, the user easily turns on the bacteria elimination shower switch. The air conditioning apparatus is a floor-mounted type, and the air outlet can be set in a mode for blowing the ions upward. Alternatively, a louver may be provided to change a direction of an ion wind blowing out.

The amount of ions generated by the ion generator in running in the bacteria elimination shower mode is preferably larger than the amount of ions generated by the ion generator in normal running except for the bacteria elimination shower mode.

The foregoing and other objects, features, aspects and advantages of the present invention will become more apparent from the following detailed description of the present invention when taken in conjunction with the accompanying drawings.

DESCRIPTION OF THE REFERENCE SIGNS

100 air cleaner, 116 upper panel portion, 123 flow path forming member, 124 inlet port, 126A and 126B air outlet, 126a and 126b louver, 130 sirocco fan, 132 motor, 134 ion generator, 136 dust sensor, 138 odor sensor, 140 front panel, 151 highly-functional filter, 152 deodorization filter, 153 formaldehyde adsorption filter, 154 antibacterial/dust filter, 160 power button, 161 ion generator switching button, 162 running mode switching button, 163 ion shower switch, 171 ion generator operating state display lamp, 172 running mode display lamp, 173 shortcut operation display lamp, 174 pollution state display unit, 174a light emitting diode, 175 ion generator operating state display unit, S1 front space, S2 rear space, 200 control device

BEST MODES FOR CARRYING OUT THE INVENTION

An air conditioning apparatus according to an exemplary embodiment of the present invention will be described in detail with reference to the drawings. In the following embodiment, a floor-mounted air cleaner having an air cleaning function is described as the air conditioning apparatus by way of example.

Figure 1:
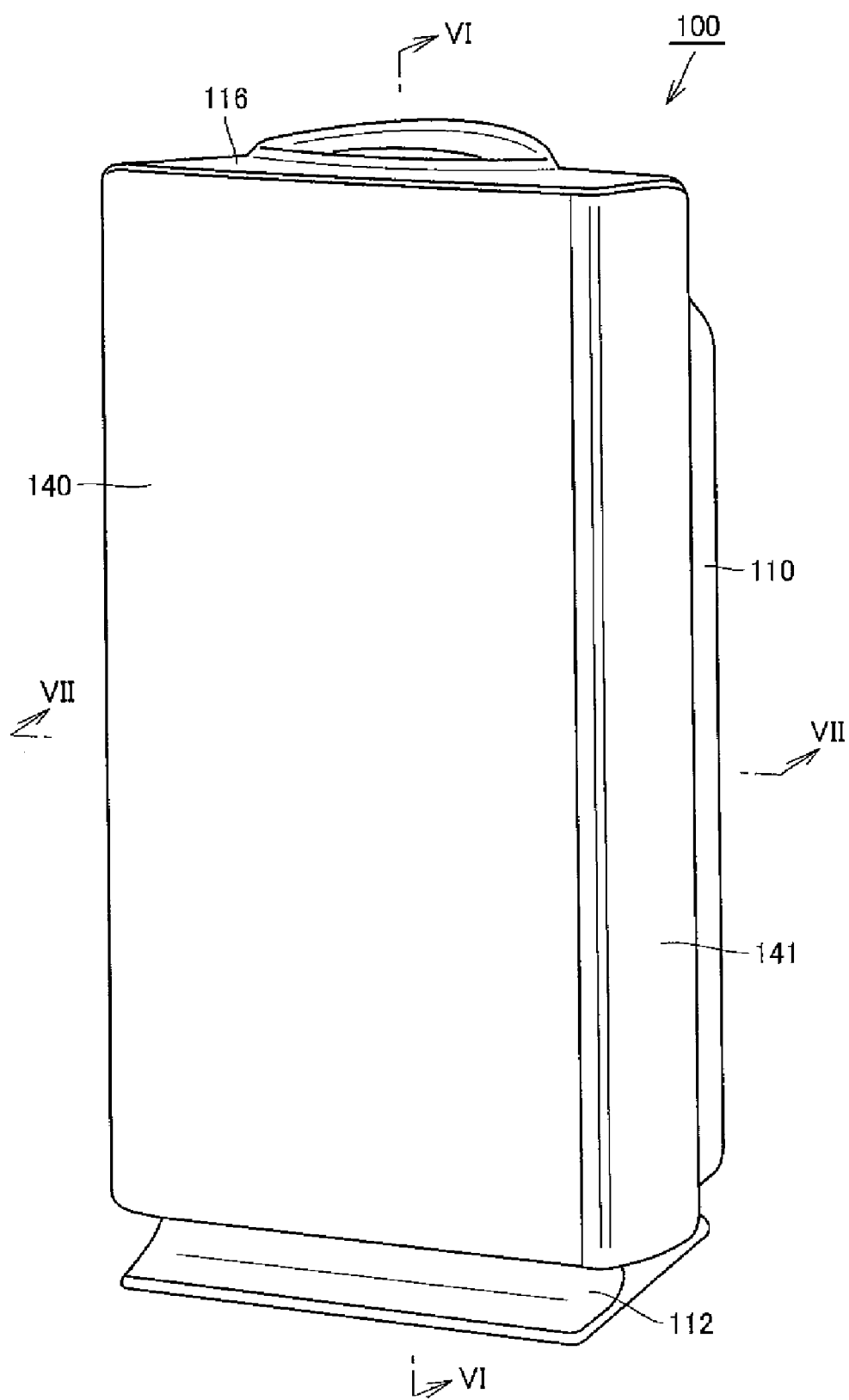
FIG. 1 is a schematic perspective view showing a front face side of an air cleaner according to an exemplary embodiment of the present invention.
Figure 2:
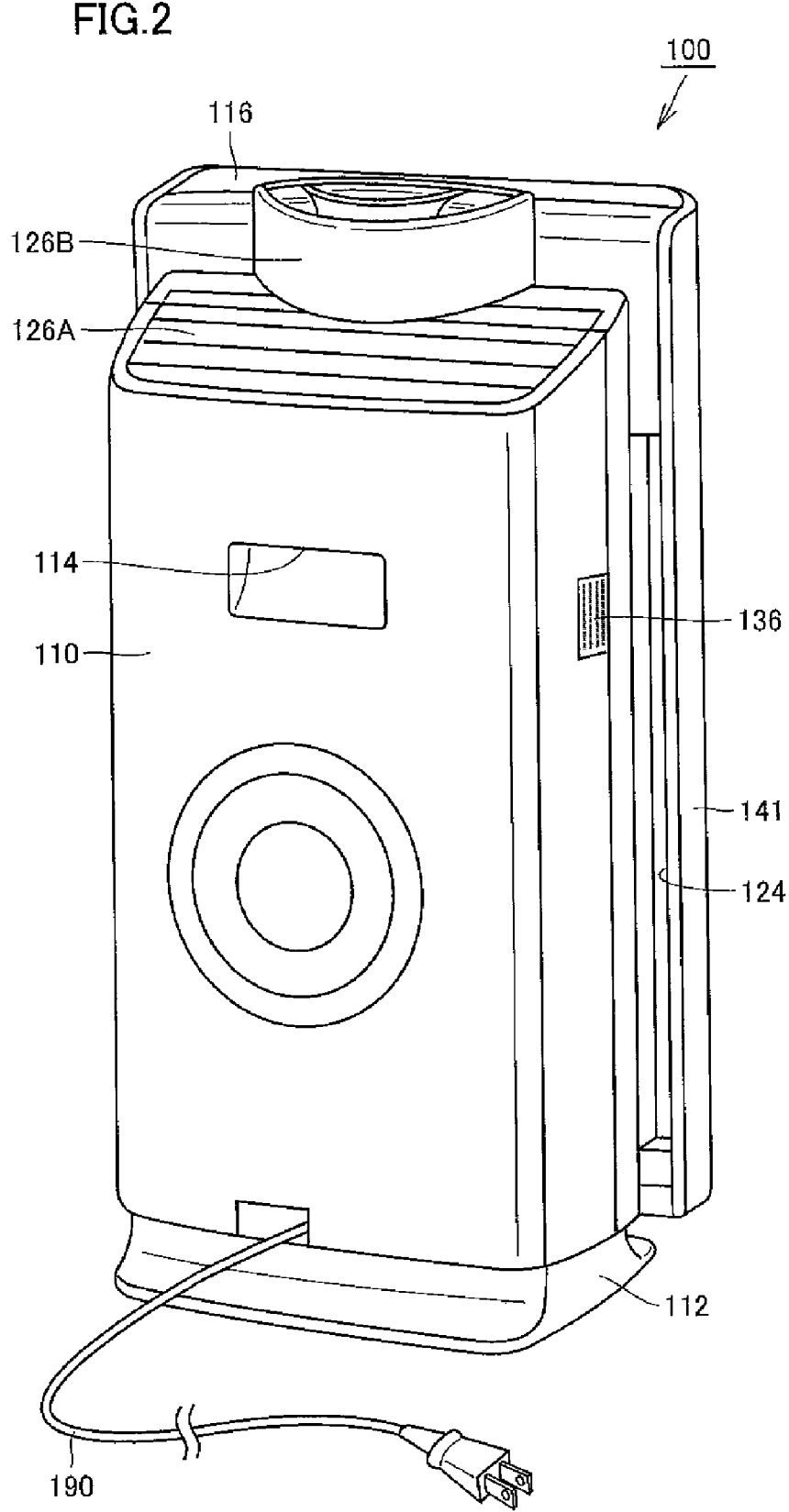
FIG. 2 is a schematic perspective view showing a rear face side of the air cleaner of the embodiment.
Figure 3:
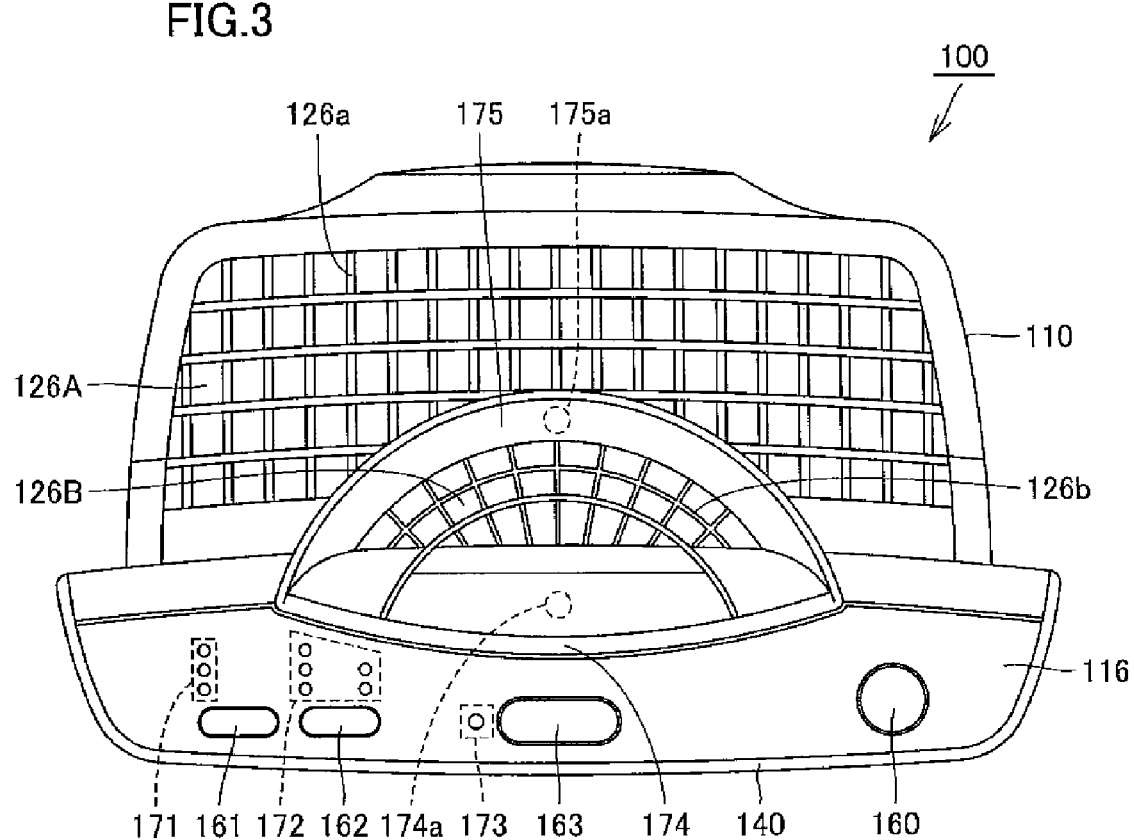
FIG. 3 is a top view showing the air cleaner of the embodiment.
Figure 4:
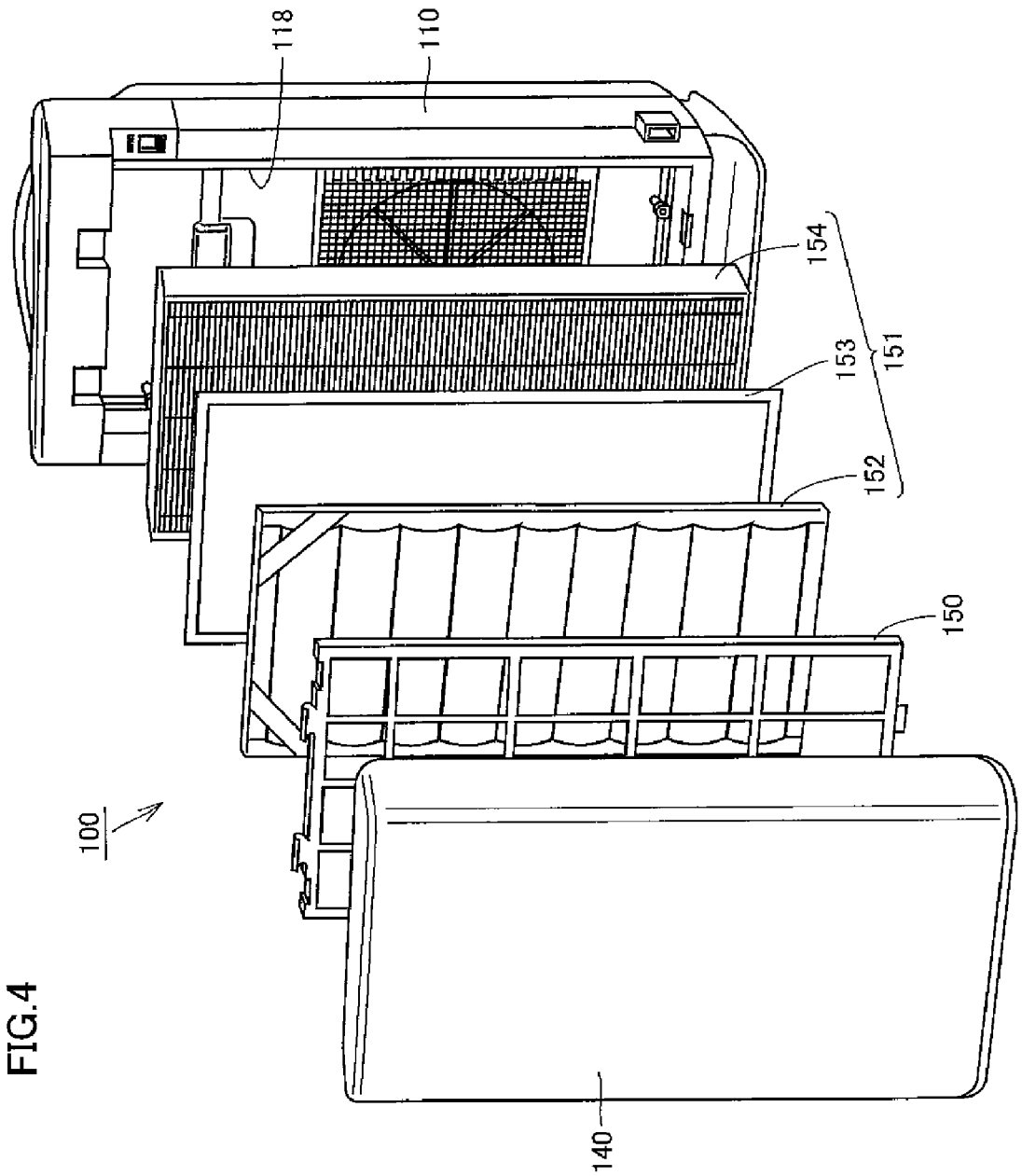
FIG. 4 is an exploded perspective view showing an assembly structure of a front panel, a filter pressing frame, and a highly-functional filter in the air cleaner of the embodiment.
Figure 5:
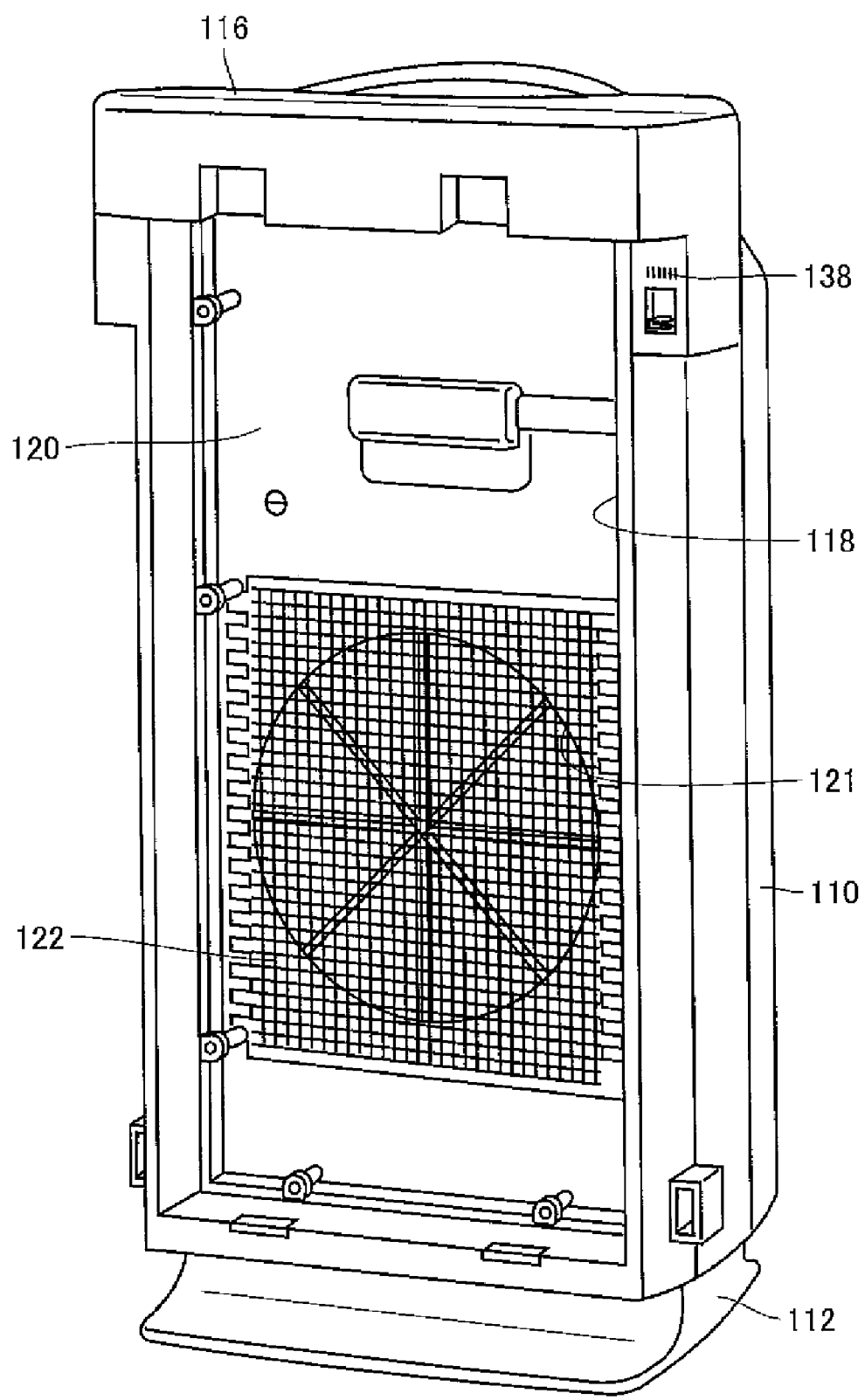
FIG. 5 is a schematic perspective view showing a state where the front panel, the filter pressing frame, and the highly-functional filter are detached from a main body casing in the air cleaner of the embodiment.

Referring to FIGS. 1 to 5, an external appearance structure of an air cleaner according to an exemplary embodiment of the present invention will be described. FIG. 1 is a schematic perspective view of the air cleaner of the embodiment when viewed from a front face side, and FIG. 2 is a schematic perspective view of the air cleaner when viewed from a rear face side. FIG. 3 is a top view of the air cleaner of the embodiment. FIG. 4 is an exploded perspective view showing an assembly structure of a front panel, a filter pressing frame, and a filter unit in the air cleaner of the embodiment, and FIG. 5 is a schematic perspective view showing a state where the front panel, the filter pressing frame, and the filter unit are detached from a main body casing in the air cleaner of the embodiment.

As shown in FIGS. 1 to 3, an air cleaner 100 of the embodiment includes a main body casing 110 and a front panel 140. Main body casing 110 is formed in a box shape whose rectangular front face is opened. Main components of air cleaner 100 are accommodated in box-shape main body easing 110. A foot portion 112 is provided below main body casing 110. Foot portion 112 is placed on a floor surface to support main body easing 110. An upper panel portion 116 is provided in an upper surface of main body casing 110, and various manipulation buttons, display lamps, and the like are provided in upper panel portion 116. Main body casing 110 may be formed by a combination of a plurality of members if needed.

A handgrip portion 114 is provided in a rear face of the main body casing 110. Handgrip portion 114 is provided in consideration of convenience when air cleaner 100 is carried. A power cord 190 is drawn from the rear face of main body easing 110.

Front panel 140 has a main face corresponding to the front face of air cleaner 100 and side portions 141 extended rearward from both side-ends of the main face. Side portion 141 is detachably attached to main body casing 110 such that parts of the front face and side faces of main body casing 110 are covered with side portion 141. Front panel 140 is a sound insulation material for preventing a noise generated in a sirocco fan or a motor from leaking to the outside of air cleaner 100 during the operation of air cleaner 100, and also ensures beautiful appearance of air cleaner 100.

As shown in FIG. 2, a gap is provided between the side face of main body casing 110 and side portion 141 of front panel 140. The gap constitutes an inlet port 124. Inlet port 124 is an opening for introducing the air from the outside into air cleaner 100. A dust sensor 136 is provided in a portion adjacent to inlet port 124.

As shown in FIGS. 2 and 3, air outlets 126A and 126B are provided in an upper portion of main body casing 110. Air outlets 126A and 126B are openings for leading the air purified in air cleaner 100 to the outside of air cleaner 100.

As described above, the various manipulating buttons and display lamps are provided in upper panel portion 116 of main body casing 110. As shown in FIG. 3, a power button 160 for switching on and off operations of air cleaner 100, a switching button 161 for switching a running state of an ion generator, and a running mode switching button 162 for switching a running mode of air cleaner 100 are provided in air cleaner 100 of the embodiment. A bacteria elimination shower switch 163 for performing running in a bacteria elimination shower mode having a predetermined high bacteria elimination effect is also provided in air cleaner 100 of the embodiment. Bacteria elimination shower switch 163 is formed larger than other buttons such that a user easily finds the bacteria elimination shower switch 163. A control device 200 is provided below upper panel portion 116, and control device 200 receives manipulation information from various manipulation buttons and controls the ion generator and sirocco fan based on the manipulation information (see FIG. 6).

In addition to these buttons, an ion generator operating state display lamp 171 for indicating a running state of the ion generator, an running mode display lamp 172 for displaying a running mode of air cleaner 100, a bacteria elimination shower mode display lamp 173 for indicating whether or not running operation in the bacteria elimination shower mode is performed, and the like also are provided in upper panel portion 116.

There are three ion generator running states displayed by operating state display lamp 171. The first state is a state where the ion generator is driven (ion automatic mode). In the first state, according to a room air pollution status detected by dust sensor 136 and odor sensor 138 (see FIG. 5), the number of positive ions and the number of negative ions are equally generated, or the number of negative ions generated is larger than the number of positive ions. The second state is a state where the ion generator is continuously driven (ion continuous mode). In the second state, the number of positive ions and the number of negative ions are equally generated. The third state is a state where the ion generator is stopped (ion stop mode). The three states are sequentially changed in each time switching button 161 is pressed. Accordingly, a user can press switching button 161 to select one of the three states according to user's preference.

There are five sirocco fan running states displayed by running mode display lamp 172. The first state is a state where a rotating speed of sirocco fan is determined according to the room air pollution status detected by dust sensor 136 and odor sensor 138 (see FIG. 5) (ion automatic mode). The second state is a state where the high-speed rotation and the normal-speed rotation of the sirocco fan are repeated (pollen mode) when pollen, dust and dirt are removed. The third state is a state where the sirocco fan is rotated at a high speed (rapid running mode) when the pollution in the air is rapidly removed. The fourth state is a state where the sirocco fan is normally rotated (standard running mode). The fifth state is a state where the sirocco fan is rotated at a low speed (silent mode) when sound generated by running of air cleaner 100 is decreased as much as possible. The five states are sequentially changed in each time running mode switching button 162 is pressed. Accordingly, the user can press running mode switching button 162 to select one of the five states according to user's preference.

Bacteria elimination shower switch 163 is a shortcut button for making transition to a specific running mode, i.e., the bacteria elimination shower mode from any running mode by one-touch manipulation. Accordingly, when bacteria elimination shower switch 163 is turned on, running is forcedly performed in the bacteria elimination shower mode, even if air cleaner 100 is stopped, or even if running is performed in a predetermined running mode. In the bacteria elimination shower mode, the rotating speed of the sirocco fan is adjusted such that the air having the air volume is blown from air outlets 126A and 126B within a range where the high bacteria elimination effect is obtained in the room. The air volume within the range where the high bacteria elimination effect is obtained in the room is a value previously obtained by experiments, and the rotating speed of the sirocco fan in the bacteria elimination shower mode is determined based on the value.

In air cleaner 100 of the embodiment, to ensure easy visibility from the front side of air cleaner 100, a pollution state display unit 174 and an ion generator operating state display unit 175 are provided while being integral with air outlet 126B projected in the upper portion of air cleaner 100. Pollution state display unit 174 visually indicates the degree of pollution of the air in the room to a user by modulating a color or brightness of a light emitting diode 174a. Light emitting diode 174a is a light source provided below pollution state display unit 174.

Pollution state display unit 174 is configured such that the display of pollution state display unit 174 is switched according to the degree of pollution of the air detected by dust sensor 136 and an odor sensor 138 (see FIG. 5). On the other hand, ion generator operating state display unit 175 visually indicates a running state of the ion generator to the user by modulating the color or brightness of a light emitting diode 175a provided below ion generator operating state display unit 175. Ion generator operating state display unit 175 is a display unit for exerting the same function as ion generator operating state display lamp 171.

As shown in FIG. 4, a highly-functional filter 151 is stored in a recess portion 118 provided on the front face side of main body casing 110. In air cleaner 100 of the embodiment, three filters of a deodorization filter 152, a formaldehyde adsorption filter 153, and an antibacterial/dust filter 154 are sequentially laminated from the front face side. A filter pressing frame 150 disposed in front of deodorization filter 152, organic matter removing filter 153, and antibacterial/dust filter 154 is fixed to the front face of main body casing 110, thereby retaining deodorization filter 152, organic matter removing filter 153, and antibacterial/dust filter 154 in recess portion 118 of main body casing 110.

As shown in FIG. 5, a communication hole 121 is made in a partition wall 120 provided at the back of recess portion 118 of main body casing 110, and a metal guard 122 is attached in front of communication hole 121. Partition wall 120 partitions an internal space of main body casing 110 into a front space S1 (see FIG. 6) and a rear space S2 (see FIG. 6), and metal guard 122 is a guard member for preventing a worker from accidentally inserting a finger into an operating fan during maintenance work. Odor sensor 138 is provided at a predetermined position in the front face of main body casing 110.

Figure 6:
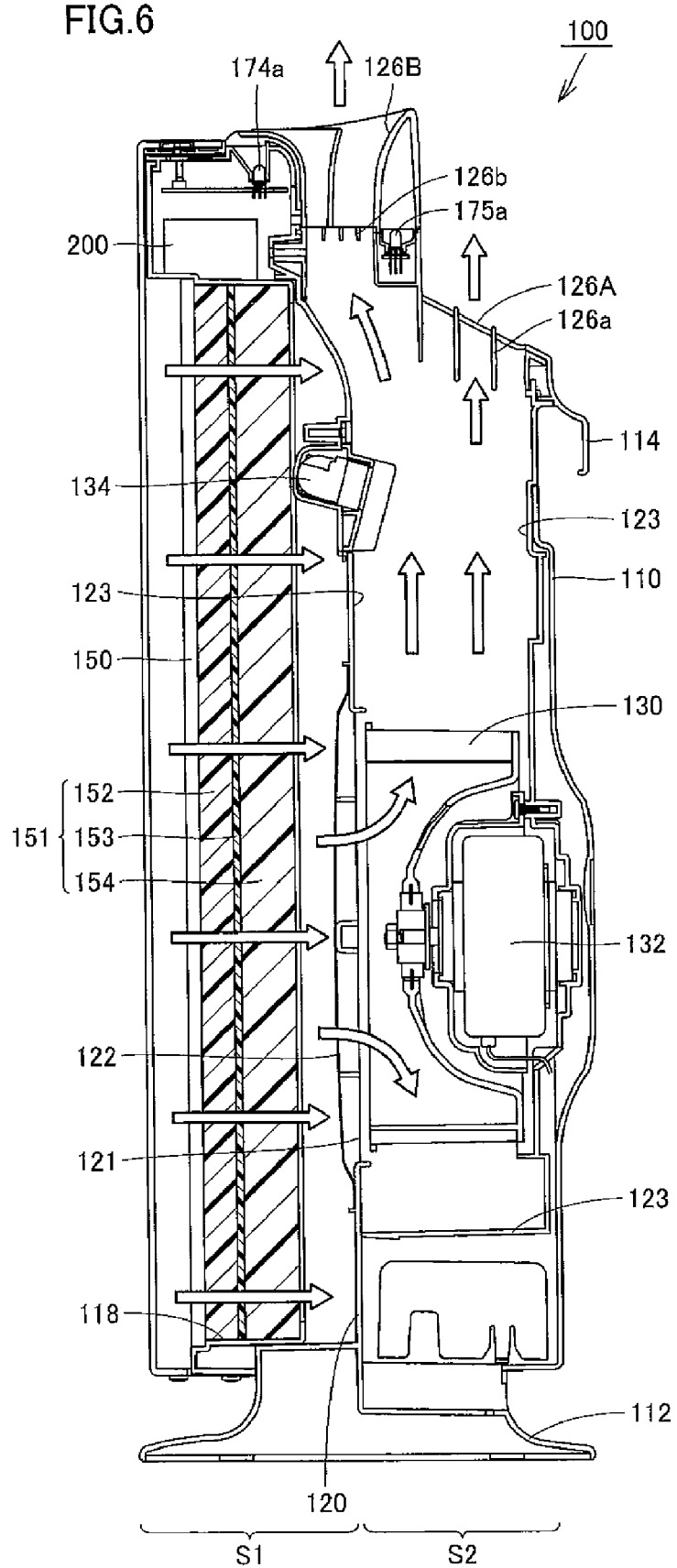
FIG. 6 is a schematic sectional view taken along a line VI-VI of FIG. 1 of the air cleaner of the embodiment.
Figure 7:
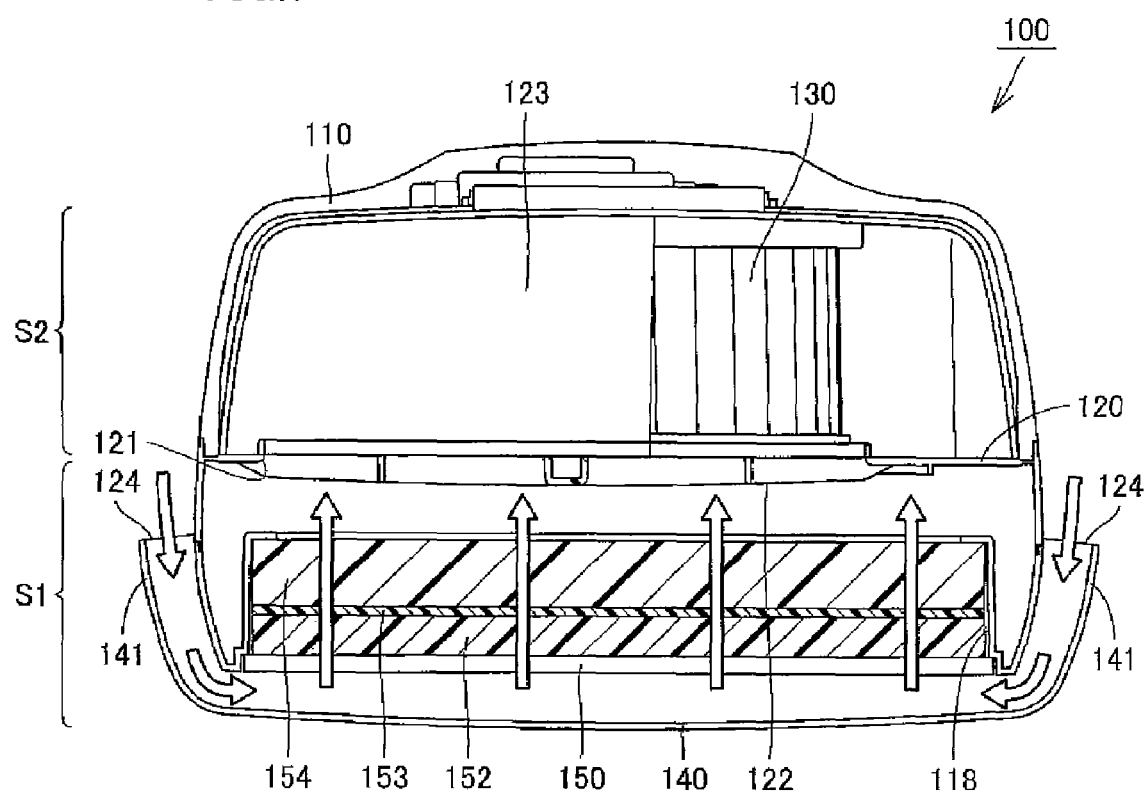
FIG. 7 is a schematic sectional view taken along a line VII-VII of FIG. 1 of the air cleaner of the embodiment.
Figure 8:
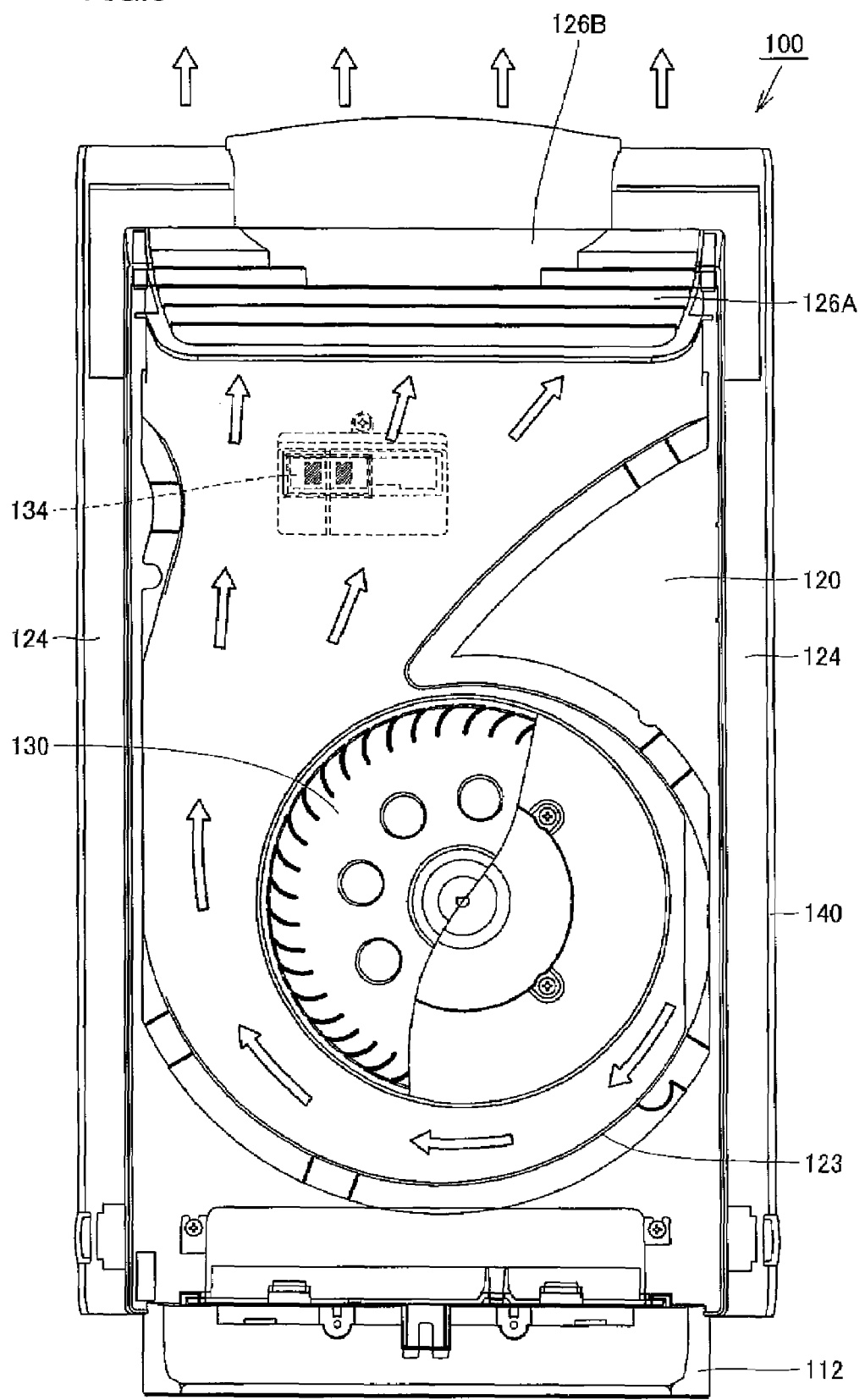
FIG. 8 is a partially broken-out rear view showing a state where a member constituting a rear portion of the main body casing is detached from the air cleaner of the embodiment.

Referring to FIGS. 6 to 8, an internal structure and an air flow of the inside in the air cleaner of the embodiment will be described below. FIG. 6 is a schematic sectional view taken along a line VI-VI of FIG. 1 of the air cleaner of the embodiment, and FIG. 7 is a schematic sectional view taken along a line VII-VII of FIG. 1. FIG. 8 is a partially broken-out sectional view showing a state where a member constituting a rear portion of the main body casing is detached in the air cleaner of the embodiment.

As shown in FIGS. 6 and 7, partition wall 120 is provided in air cleaner 100. Highly-functional filter 151 including deodorization filter 152, formaldehyde adsorption filter 153, and antibacterial/dust filter 154 is disposed in front of partition wall 120, and front panel 140 is disposed in front of highly-functional filter 151. Highly-functional filter 151 divides a front space S1 located between front panel 140 and partition wall 120 into two in a depth direction, and the divided spaces constitute air flow paths respectively. As shown in FIG. 7, front space S1 is communicated with the outside of air cleaner 100 through inlet port 124 in the side face of main body casing 110.

As shown in FIGS. 6 to 8, a sirocco fan 130 is disposed at the back of partition wall 120. Sirocco fan 130 is rotated by a motor 132 disposed at the back of sirocco fan 130. Communication hole 121 in partition wall 120 is made so as to face a suction surface of sirocco fan 130.

A rear space S2 of main body casing 110 is communicated with air outlets 126A and 126B provided in the upper portion of main body casing 110. Louvers 126a and 126b are provided in air outlet 126A and 126B respectively. Louvers 126a and 126b are used to align an orientation of the air blown from air outlet 126A and 126B. Accordingly, a user places air cleaner 100 near a wall of the room while the rear face of air cleaner 100 faces the wall, and attitudes of louvers 126a and 126b are changed to blow the air from air outlets 126A and 126B toward an obliquely upward direction on the side of front panel 140, thereby effectively forming the ion shower to fall to the floor surface. However, even if the air is blown immediately above from air outlets 126A and 126B, the ion shower is formed by an air stream formed in the room.

A flow path forming member 123 is disposed in rear space S2 of main body casing 110. Flow path forming member 123 is used to guide the air flow introduced in rear space S2 by sirocco fan 130 to air outlets 126A and 126B, and forms an air flow path in rear space S2 along with partition wall 120. Flow path forming member 123 is formed in a shape to surround sirocco fan 130 in a lower portion thereof and guide the air blown from sirocco fan 130 to air outlets 126A and 126B in an upper portion thereof.

An ion generator 134 is provided at a predetermined position of partition wall 120 facing rear space S2. Ion generator 134 emits the positive ions and the negative ions to the air passing through rear space S2. In ion generator 134, oxygen or moisture in the air is ionized by applying an alternating-current voltage between electrodes provided in an ion generating element. An ion emitting surface of ion generator 134 is disposed so as to face the inside of flow path forming member 123, whereby the generated ions are let to the outside of air cleaner 100 along with the air flow.

The ions generated by ion generator 134 include the positive ions and the negative ions. The positive ions and the negative ions adhere alternatively to the surfaces of the airborne fungi, bacteria, and viruses to form hydroxide ions, and the hydroxide ions remove hydrogen ions from cell walls of the fungi, bacteria, and viruses to break the cell walls, thereby killing the fungi, bacteria, and viruses. Accordingly, in air cleaner 100 of the embodiment, because the positive ions and the negative ions are blown out of air outlets 126A and 126B such that extinction of the ions is hardly generated by recombination of the ions, a partition plate is provided between the electrode for generating the positive ions and the electrode for generating the negative ions. Although the ion generator for generating both the positive ions and the negative ions is used in the embodiment, the ion generator for generating either the positive ions or the negative ions may be used as long as the ion generator can generate the ions having the bacteria elimination function.

In air cleaner 100 having the above-described configuration, sirocco fan 130 is driven by motor 132 to generate a negative pressure in front space S1 of main body casing 110, and the air in the room is taken in front space S1 through inlet port 124 laterally located in the main body casing 110 (see FIG. 7). When the air taken in front space S1 passes through highly-functional filter 151, the deodorization process, the formaldehyde adsorbing process, the duct trapping process, and the antibacterial process are performed to the air. Then, the air passes through communication hole 121 made in partition wall 120, and the air is introduced to rear space S2 (see FIGS. 6 and 7).

The air flowing in rear space S2 is blown toward the outside from a peripheral surface portion of sirocco fan 130. The air blown from sirocco fan 130 is guided to flow path forming member 123, the air is raised in rear space S2, and the air is blown out to the room through air outlets 126A and 126B while ion generator 134 adds the positive ions and/or negative ions having a predetermined concentration (see FIGS. 6 and 7). In FIGS. 6 to 8, the air flow is indicated by arrows.

Figure 9:
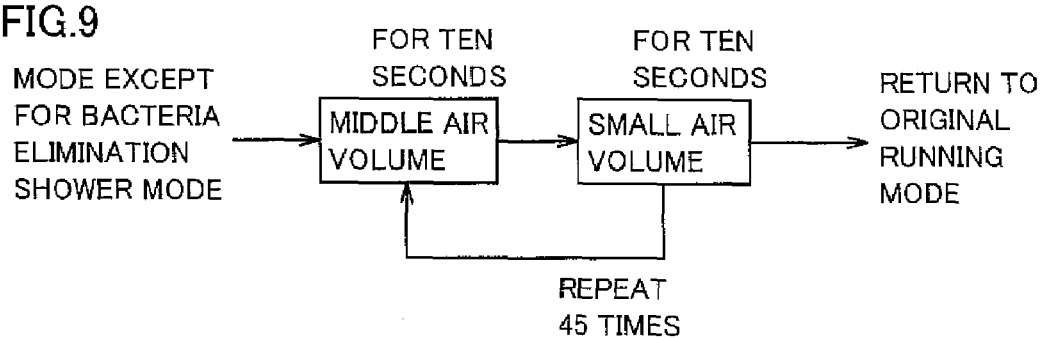
FIG. 9 is a view showing a control flow of bacteria elimination shower running.

In air cleaner 100 of the embodiment, as shown in FIG. 9, when the bacteria elimination shower switch is turned on, running is forcedly changed from other modes (including a stopped state of air cleaner 100) to the bacteria elimination shower mode. In the bacteria elimination shower mode, for example, sirocco fan 130 is put in motion for ten minutes while the rotating speed is set to a middle air volume, and then sirocco fan 130 is put in motion for ten minutes while the rotating speed is set to the small air volume. For example, a first air volume control of the middle air volume and a second air volume control of the small air volume are repeated 45 times. Then, the mode except for the bacteria elimination shower mode is performed again before the bacteria elimination shower switch is turned on.

The following is the reason why the air volume of the blower is controlled as described above in the bacteria elimination shower mode.

In the above control, when bacteria elimination shower switch 163 is turned on, control device 200 forcedly drive ion generator 134 in any control state at that time. At this point, because ion generator 134 generates a larger amount of ions than that of the ions generated in a normal running state (the ion automatic mode and the ion continuous mode) except for a running state in the bacteria elimination shower mode, the number of times of discharging per unit time is increased compared to the normal running state while the same voltage is applied to the electrodes. For example, in running in the bacteria elimination shower mode, ion generator 134 performs discharging ten times of the number of times in the normal running (per unit time) such that the ions are generated at least double the normal running (per unit time).

Additionally, control device 200 controls the rotating speed of sirocco fan 132 such that the air flow is generated within a predetermined range. Accordingly, the user presses only the bacteria elimination shower switch to generate the air flow having the air volume suitable for enhancement of the bacteria elimination effect, and the bacteria elimination effect can be improved.

Control device 200 desirably controls sirocco fan 132 such that the air flow having the air volume smaller than the maximum air volume (the air volume in the rapid running mode) sirocco fan 132 can generate.

Figure 10:
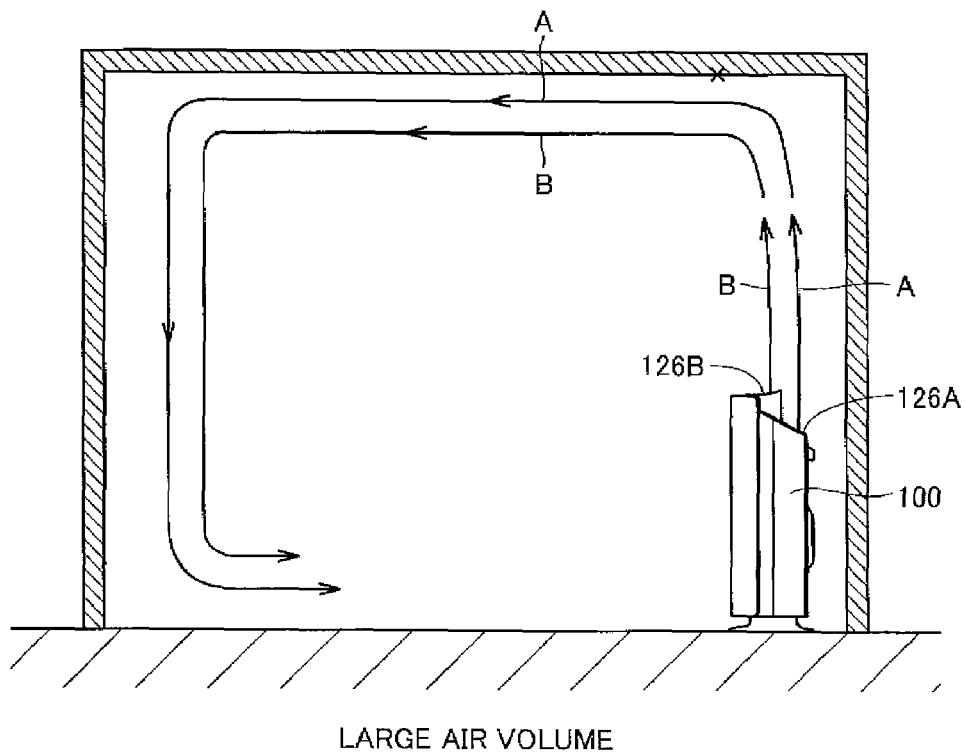
FIG. 10 is a view showing an air flow blown from an air conditioning apparatus whose blower has a large air volume.

In the control performed by air cleaner 100, in general a large air volume is desirably generated by sirocco fan 132 in consideration of a pollution substance removing effect. However, as in the above-described control, when sirocco fan 132 is controlled to generate the air flow having the air volume for easily obtaining the bacteria elimination effect smaller than the maximum air volume (the air volume in the rapid running mode) sirocco fan 132 can generate, collision of the air including the positive ions and negative ions blown from air outlets 126A and 126B with the ceiling or the wall is suppressed as shown in FIG. 10, thereby suppressing disappearance of the ions. Therefore, when bacteria elimination shower switch 163 is turned on, control device 200 performs the control to run sirocco fan 132 at a predetermined rotating speed such that the air volume, e.g., within the range of 540 rpm to 780 rpm, is generated. Accordingly, the positive ions and negative ions blown from air outlets 126A and 126B easily fall to the floor surface without disappearance.

Figure 11:
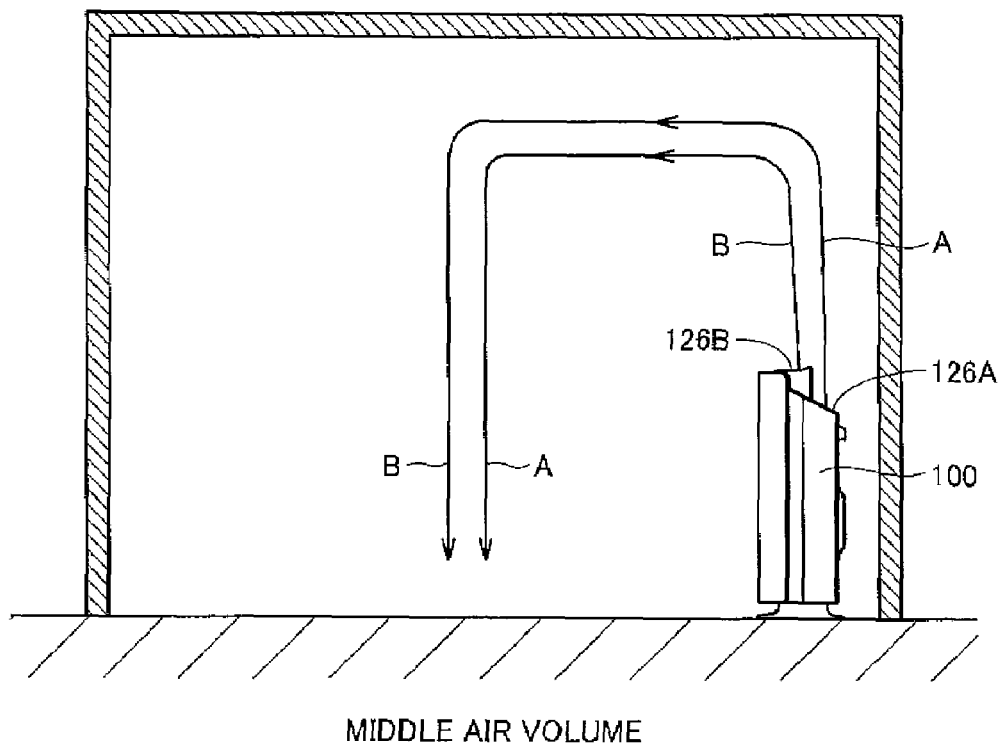
FIG. 11 is a view showing an air flow blown from an air conditioning apparatus whose blower has a middle air volume.

For example, in a case where the first air volume control having the middle air volume (780 rpm) is performed, as shown by arrows A and B in FIG. 11, an air flow B including the positive ions and negative ions blown upward (or obliquely upward) from air outlet 126B reaches a position relatively away from air cleaner 100 without colliding with the ceiling and wall surface in the inside of a flow A of only the air blown out of air outlet 126A to act as an air curtain.

In air cleaner 100 of the embodiment, either the control for enhancing the bacteria elimination effect or the control for enhancing the pollution substance removing effect in the air can be selected and performed.

Control device 200 desirably controls sirocco fan 132 such that sirocco fan 132 generates the air flow having the air volume larger than the minimum air volume (the air volume in the silent mode) sirocco fan 132 can generate.

In the control performed by air cleaner 100, in general the small air volume is desirably generated by sirocco fan 132 in consideration of a noise generated by air cleaner 100. However, according to the above-described control, sirocco fan 132 is controlled so as to generate the air flow having the air volume larger than the minimum air volume (the air volume in the silent mode) sirocco fan 132 can generate. Therefore, the amount of positive ions and negative ions blown from air outlets 126A and 126B is not decreased less than the minimum amounts for obtaining the appropriate bacteria elimination effect, so that the high bacteria elimination effect can be obtained according to the above-described control.

Figure 12:
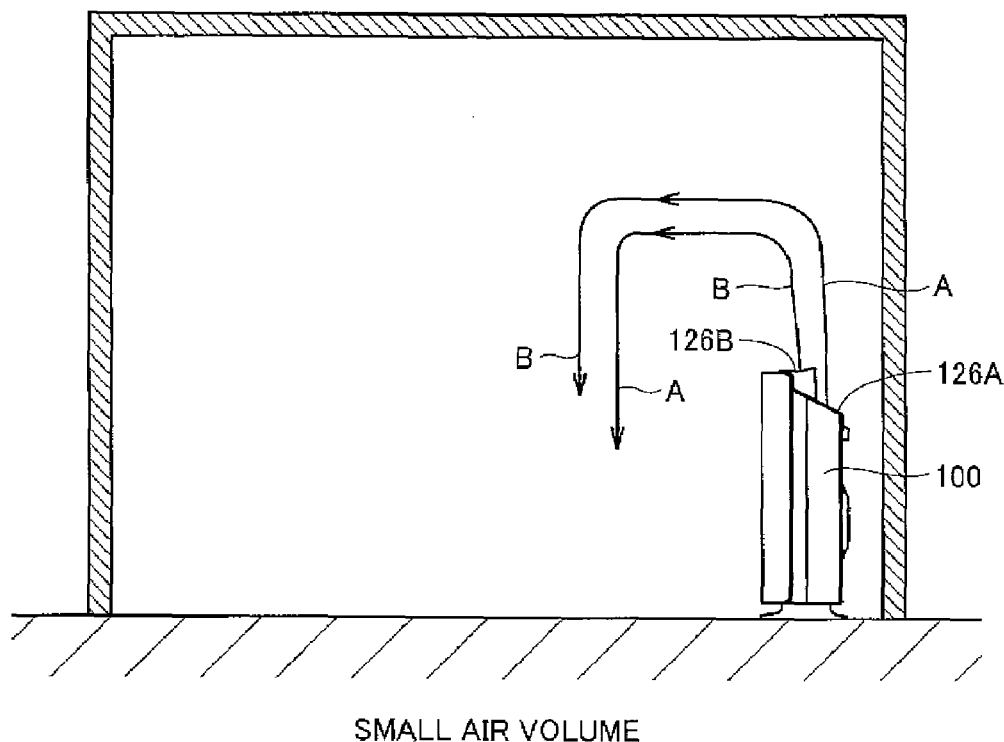
FIG. 12 is a view showing an air flow blown from an air conditioning apparatus whose blower has a small air volume.

For example, in a case where the second air volume control with the air volume (540 rpm) that is smaller than that of the first air volume control is performed, air flow B including the positive ions and negative ions and flow A of only the air reach the position relatively close to air cleaner 100 as shown by arrows A and B in FIG. 12.

That is, in air cleaner 100 of the embodiment, either the control for the silent mode or the control for enhancing the bacteria elimination effect can be selected and performed.

In the conventional air cleaner, the control is not performed such that the positive ions and the negative ions are blown while dispersed in the room. Accordingly, because the positive ions and the negative ions fall intensively to a predetermined position in the room, sometimes the bacteria elimination is performed only at the predetermined position in the room while hardly performed in other places. In other words, because the conventional air cleaner cannot evenly perform the bacteria elimination in the room, sometimes the bacteria elimination effect becomes decreased.

On the contrary, according to the control performed by air cleaner 100 of the embodiment, in the bacteria elimination shower mode, the positive ions and the negative ions are blown out upward from air outlet 126A while the air volume of the sirocco fan 130 is automatically changed. That is, the positive ions and the negative ions are blown away from air cleaner 100 or falls near air cleaner 100. In other words, the positive ions and the negative ions do not fall intensively to the predetermined position in the room, but the positive ions and the negative ions fall to a plurality of positions in a dispersed manner. Accordingly, the user can press only bacteria elimination shower switch 163 to easily perform the even bacteria elimination in the room.

The air volume can automatically be changed to intensively perform the bacteria elimination of a region within a predetermined range in the room with the small air volume.

In the embodiment, control device 200 repeats the first air volume control and the second air volume control for a predetermined time, e.g., ten minutes as shown in FIG. 9, so that the even bacteria elimination can further be performed in the room.

As shown in FIG. 9, in the embodiment, control device 200 performs the same control as that performed immediately before bacteria elimination shower switch 163 is turned on when running in the bacteria elimination shower mode is ended. Even if the user does not manipulate any switch, air cleaner 100 automatically returns to a state immediately before bacteria elimination shower switch 163 is turned on, so that user's convenience can be improved.

Because the bacteria elimination shower switch 163 is larger than other switches, the user easily turns on bacteria elimination shower switch 163.

In the embodiment, the floor-mounted air cleaner is illustrated as the air conditioning apparatus, and the air is flown from air outlets 126A and 126B toward the obliquely upward direction on the front face side along with the positive ions and the negative ions. However, the present invention is not limited to the floor-mounted air cleaner. The air conditioning apparatus of the present invention shall include a general indoor apparatus, used in a general room, for introducing the air from the outside of the apparatus to the inside and delivering the air to the outside after a certain process is performed to the introduced air. Accordingly, in addition to the floor-mounted air cleaner, the air conditioning apparatus shall include a wall-hung air cleaner, a built-in air cleaner, an in-car air cleaner, an air harmonic generator, a dehumidifier, a humidifier, an electric heater, an oil stove, an oil fan heater, a gas heater, a refrigerator, a cooler box, an air conditioning duct for building, and an in-car air conditioning duct. That is, the present invention can be applied to any air conditioning apparatus as long as the orientation of the sir blown from the air outlet can be adjusted to improve the elimination shower effect according to the installation position in the room and an ambient environment.

Although the present invention has been described and illustrated in detail, it is clearly understood that the same is by way of illustration and example only and is not to be taken by way of limitation, the spirit and scope of the present invention being limited by the terms of the appended claims.

The invention claimed is:

1. A floor-mounted air conditioning apparatus comprising:
an ion generator to generate ions;
a flow path forming member including said ion generator, to cause air to flow;

a blower to cause the air to flow in said flow path forming member;

an ion outlet disposed in an end portion of said flow path forming member, to blow said ions along with air flowing around said ion generator disposed on one inner wall surface of said flow path forming member;

an air outlet to blow air flowing near another inner wall surface of said flow pat forming member;

a louver disposed at said air outlet to change an air flow;

a switch to switch over a driving state of said ion generator;

a bacteria elimination shower switch to cause said ion generator to run in a bacteria elimination shower mode where said ion generator generates an amount of ions larger than a normally generated amount of ions according to switching over of said switch;

a control device to control said blower; and an inlet port to introduce air into an inside from an outside of said air conditioning apparatus, wherein when said air conditioning apparatus is disposed near a wall such that said air outlet is brought relatively closer to said wall rather than said ion outlet while said inlet port is kept relatively away from said wall rather than said ion outlet, the air blown from said air outlet flows so as to cover, from an outside, an air flow including ions blown from said ion outlet, and when said bacteria elimination shower switch is turned on while air is blown immediately upward or obliquely upward by said louver, said control device forcibly drives said ion generator in said bacteria elimination shower mode irrespective of a control state at that time, repeats, for a predetermined number of times, control to automatically change magnitudes of air volumes blown from said air outlet and said ion outlet within a predetermined range, and controls said blower so as to generate air flows including said ions in a dispersed manner into a plurality of positions in a room.

2. The air conditioning apparatus according to claim 1, further comprising a fiber to be able to collect a pollution substance in the air, wherein said blower sucks the air through said filter and causes the air to flow into said flow path forming member after the pollution substance is removed by said filter, and said control device controls said blower such tat said blower generates the air flow having an air volume smaller than a maximum air volume said blower can generate when said bacteria elimination shower switch is turned on.

3. The air conditioning apparatus according to claim 1, wherein said control device controls said blower such that said blower generates the air flow having an air volume larger than a minimum aft volume said blower can generate when said bacteria elimination shower switch is turned on.

4. The air conditioning apparatus according to claim 1, wherein said control device performs first air volume control for causing said blower to generate the air flow having a predetermined air volume and second air volume control for causing said blower to generate the air flow having an air volume smaller than said predetermined air volume, when said bacteria elimination shower switch is turned on.

5. The air conditioning apparatus according to claim 4, wherein said control device repeats said first air volume control and said second air volume control.

6. The air conditioning apparatus according to claim 1, wherein said control device performs control identical to control performed immediately before said bacteria elimination shower switch is turned on, when running in said bacteria elimination shower mode is ended.

* * * * *